(12) United States Patent
Lee

(10) Patent No.: US 7,104,266 B2
(45) Date of Patent: Sep. 12, 2006

(54) FLOSSING TOOL

(76) Inventor: Chee Yin Lee, 24H Po Yang Mansion Tai, Koo Shing (HK)

( * ) Notice: Subject to any disclaimer, the term of this patent is extended or adjusted under 35 U.S.C. 154(b) by 230 days.

(21) Appl. No.: 10/454,123

(22) Filed: Jun. 4, 2003

(65) Prior Publication Data

US 2004/0244815 A1   Dec. 9, 2004

Related U.S. Application Data

(63) Continuation-in-part of application No. 10/163,922, filed on Jun. 5, 2002, now abandoned.

(51) Int. Cl.
 *A61C 16/04* (2006.01)
(52) U.S. Cl. .................................................... 132/323
(58) Field of Classification Search ......... 132/321–327
 See application file for complete search history.

(56) References Cited

U.S. PATENT DOCUMENTS

| | | | | |
|---|---|---|---|---|
| 2,873,749 A | * | 2/1959 | Gjerde ........................ | 132/323 |
| 3,718,146 A | * | 2/1973 | Myers ......................... | 132/326 |
| 3,870,059 A | * | 3/1975 | Bennington ................. | 132/325 |
| 3,871,393 A | * | 3/1975 | Wharton ...................... | 132/326 |
| 3,882,879 A | * | 5/1975 | Lucas .......................... | 132/326 |
| 3,886,956 A | * | 6/1975 | Cash ........................... | 132/325 |
| 3,903,907 A | * | 9/1975 | Knaus .......................... | 132/326 |
| 4,655,233 A | * | 4/1987 | Laughlin ...................... | 132/323 |
| 4,832,062 A | * | 5/1989 | Grollimund et al. ......... | 132/327 |
| D319,325 S | * | 8/1991 | Green .......................... | D28/68 |
| 5,139,038 A | * | 8/1992 | El Gazayerli ................ | 132/325 |
| 5,423,338 A | * | 6/1995 | Hodge et al. ................. | 132/324 |
| 5,482,466 A | | 1/1996 | Haynes | |
| 5,560,378 A | * | 10/1996 | Tiphonnet ..................... | 132/325 |
| 5,782,250 A | | 7/1998 | Harrah, Jr. | |
| 6,092,536 A | | 7/2000 | Owens | |
| 6,209,550 B1 | | 4/2001 | Powell, Jr. | |

* cited by examiner

*Primary Examiner*—Kevin Shaver
*Assistant Examiner*—Stephanie Willatt
(74) *Attorney, Agent, or Firm*—Jackson Walker, LLP

(57) ABSTRACT

A flossing tool, for use with flossing string, includes a handle having a forked head at its first end. The forked head has first and second arms extending outwardly to first and second distal ends for supporting flossing string therebetween. A tensioner is slidably disposed on the handle and includes a clamp for receiving ends of the flossing string. The tensioner is movably between a first position wherein the flossing string is freely receivable in the clamp and a second position wherein the flossing string is secured in the clamp.

11 Claims, 6 Drawing Sheets

FLOSSING TOOL

This is a continuation-in-part application of U.S. patent application Ser. No. 10/163,922, filed 5 Jun. 2002, now abandoned.

BACKGROUND TO THE INVENTION

1. Field of the Invention

The invention relates to flossing teeth and in particular to flossing tools adapted to hold floss string to assist a person flossing teeth.

2. Background Information

Numerous flossing tools designed to hold flossing string are known. Examples are described in U.S. Pat. No. 6,209,550; U.S. Pat. No. 6,092,536; U.S. Pat. No. 5,782,250 and U.S. Pat. No. 5,482,466. A problem with these flossing tools, and many others, is that a high degree of skill and dexterity is required to manipulate the flossing string on the tool.

SUMMARY OF THE INVENTION

It is an object of the present invention to provide a flossing tool that is easy to use, or which at least ameliorates problems with known flossing tools. It is a further object of the present invention to at least provide the public with a useful alternative.

According to a first aspect of the invention there is provided a flossing tool for use with flossing string, the flossing tool including:

a handle having first and second ends;

a head at the first end of the handle and having a first arm extending outwardly to a first distal end and a second arm extending outwardly to a second distal end, the first and second distal ends adapted to support flossing string therebetween, and a tensioner slidably disposed on the handle and having a clamp, the tension being movable between a first position for freely receiving ends of the flossing string in the clamp and a second position for securing the ends of the flossing string in the clamp.

Preferably, the first arm has a first groove for guiding the flossing string to the first distal end, and second arm has a second groove for guiding the flossing string to the second distal end.

Preferably, the first and second arms extend outwardly away from each other.

Preferably, the first and second arms resiliently deform inwardly towards each other.

Preferably, the handle has a channel extending from proximate its first end towards its second end for slidably receiving the tensioner.

Preferably, the first and second distal ends have a split eye.

Preferably, the flossing tool further includes a cartridge releasably mounted to the handle for holding flossing string.

Preferably, the cartridge comprises first and second housing elements releasably joined at an equator, and an opening through which flossing string can pass.

Preferably, the opening is provided with a blade for cutting the flossing string.

According to a second aspect of the invention there is provided a flossing tool for use with flossing string, the flossing tool including:

a handle portion having a first end and a second end;

a head at the first end of the handle and having a first arm extending outwardly to a first distal end and a second arm extending outwardly to a second distal end, the first and second distal ends adapted to support flossing string there between, a channel extending between the first and second ends of the handle, and a tensioner slidably positioned with the channel and having a clamp, the tension being movable between a first position for freely receiving ends of the flossing string in the clamp and a second position for securing the ends of the flossing string in the clamp and tensioning the flossing string between the first and second distal ends.

Further aspects of the invention will become apparent from the following description, which is given by way of example only.

BRIEF DESCRIPTION OF THE DRAWINGS

Embodiments of the invention will now be described with reference to the accompanying drawings in which.

DESCRIPTION OF THE PREFERRED EMBODIMENTS

Figure 1:
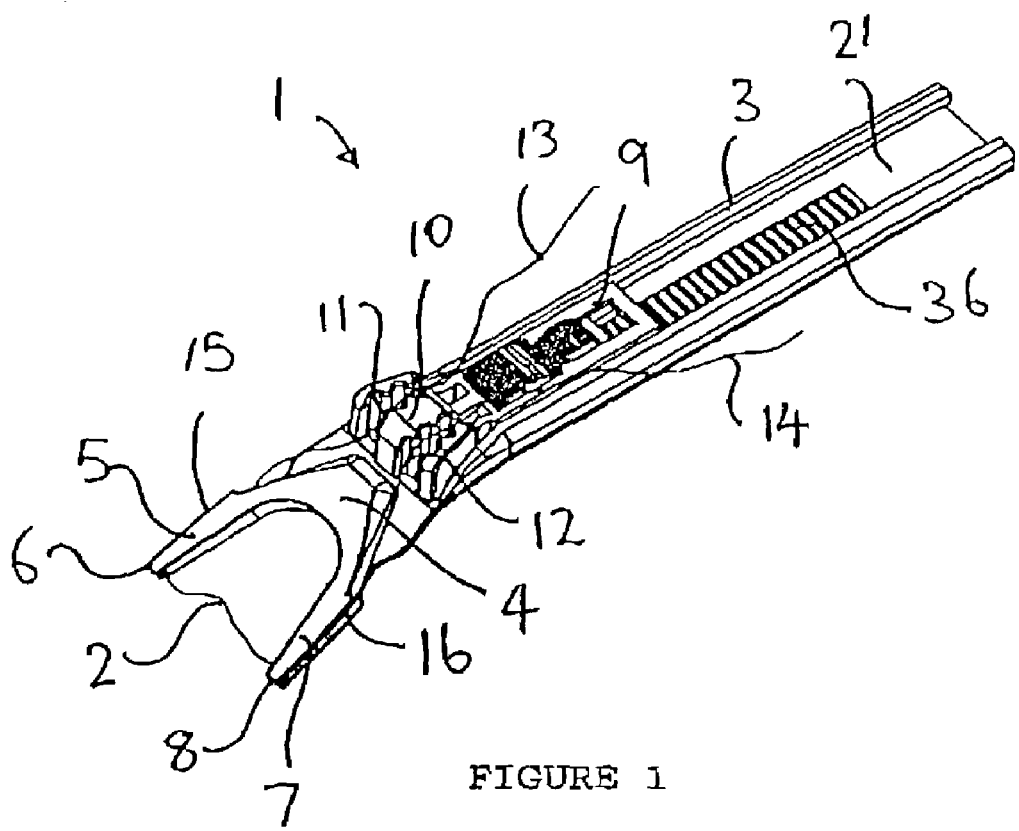
FIG. 1 illustrates a first perspective view of a flossing tool according to the invention.
Figure 2:
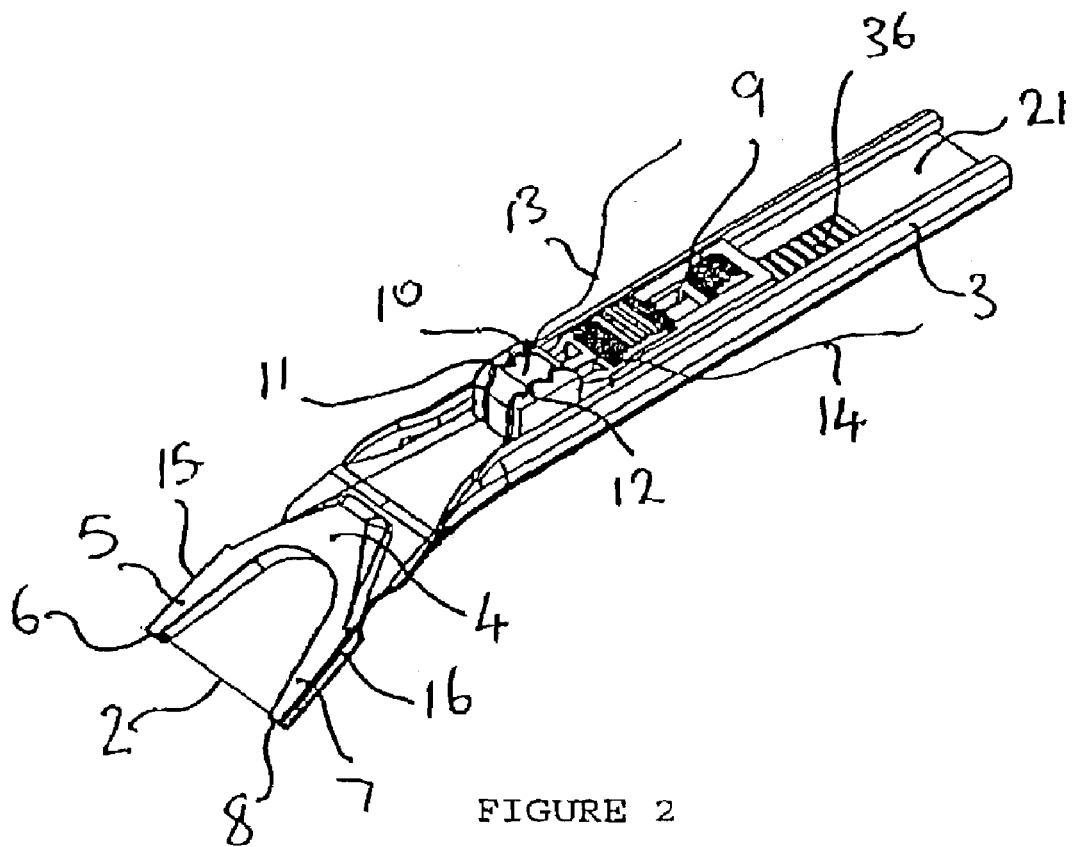
FIG. 2 illustrates a second perspective view of the flossing tool.
Figure 3:
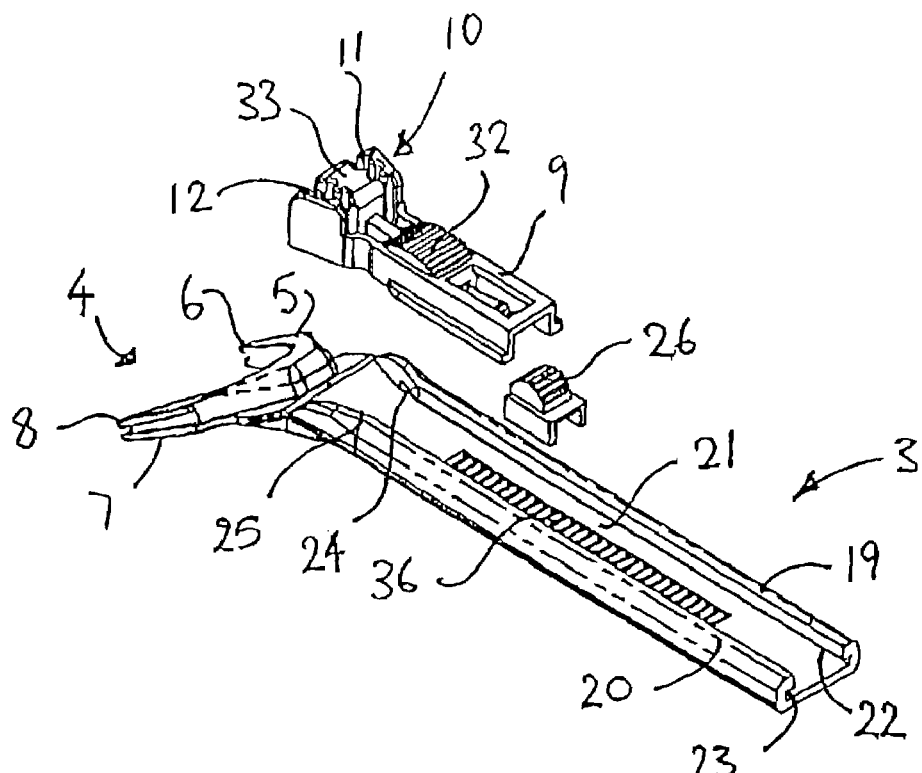
FIG. 3 illustrates an exploded perspective view of the flossing tool.

Referring to FIGS. 1 to 3, a flossing tool 1 for use with a length of flossing string 2 includes a handle 3 extending to a forked head 4 at its first end. The forked head 4 has a first arm 5 extending outwardly to a first distal end 6 and a second arm 7 extending outwardly to a second distal end 8. In use, the flossing string 2 is supported between the first and second distal ends 6, 8 of the arms. The outer edges of each of first and second arm portions 5, 7 has a groove 15, 16 for guiding flossing string 2 along each arm 5, 7 to distal ends 6, 8.

A tensioner 9 is slidably disposed on the handle 3. The tensioner 9 includes a clamp 10 with side-by-side jaws 11, 12 through which ends 13, 14 of the flossing string 2 pass. Tensioner 9 is slidable between a first position adjacent head 4 as shown in FIG. 1 and a second position away from the head 4 as shown in FIG. 2.

Figure 4:
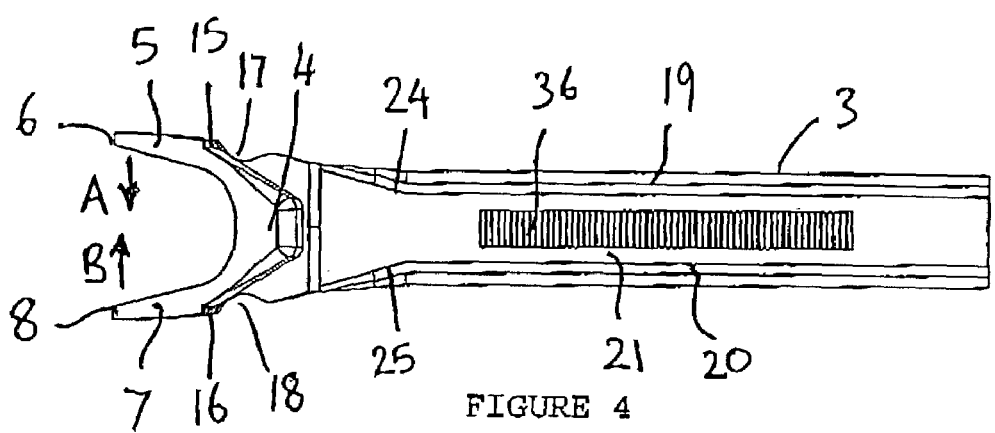
FIG. 4 illustrates a plan view of a handle and head portion of the flossing tool.
Figure 5:
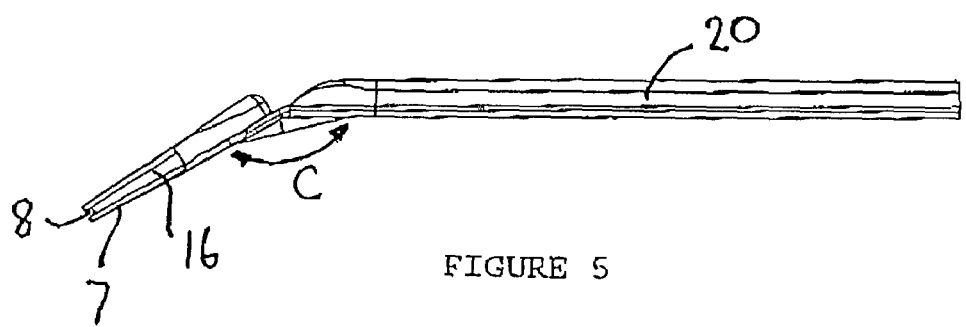
FIG. 5 illustrates a side elevation view of the handle and head portion.

Referring to FIGS. 4 and 5, the handle 3 and head 4 are integrally formed with head 4 orientated at an angle C from handle 3 to facilitate a comfortable operating position. The first and second arm members 6, 7 are integrally formed branches of the forked head 4. In the preferred embodiment the first and second arms 6, 7 are formed to extend outwardly away from each other so that operating area between distal ends 6, 8 is greater than the nominal width of head 4.

The handle 3 and head 4 are made of well-known thermoplastic elastomers (TPEs) to provide flexibility with good elastic recovery properties. When under tension first and second arms 6, 7 flex inwardly towards each other as shown by arrows A and B. To help facilitate the flex each arm 5, 6 has a semi-circular shaped notch 17, 18 at is proximal end adjacent head 4. When tension is released from arms 5, 6 they return to their outwardly extending positions.

The longitudinal edges 19, 20 of handle 3 are rolled upwardly and inwardly to form a channel 21, with grooves 22, 23 along its internal edges, longitudinally in the handle 3. Proximate the head 4 the channel 21 opens to a mouth with edges 19, 20 forming rounded entrance shoulders 24, 25. Within the floor of channel 21 are formed 'saw-tooth' shaped locking teeth 36.

Figure 6:
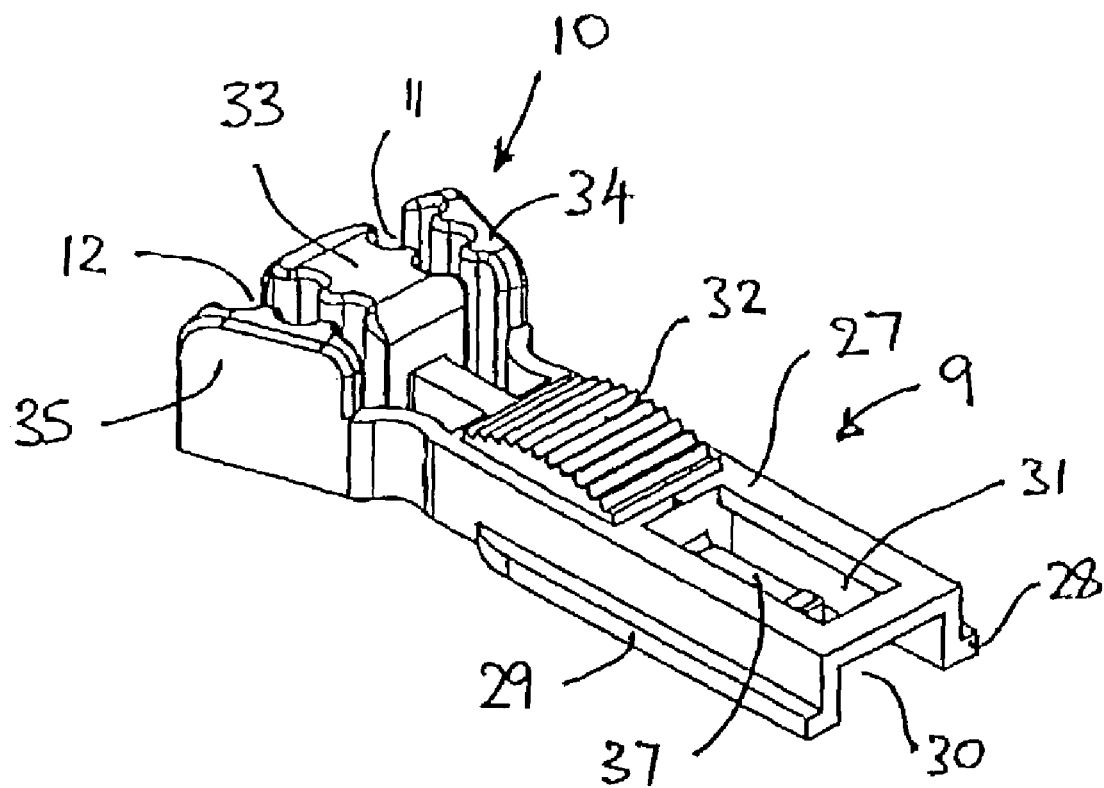
FIG. 6 illustrates a perspective view of a tensioner and clamp portion of the flossing tool.
Figure 7:
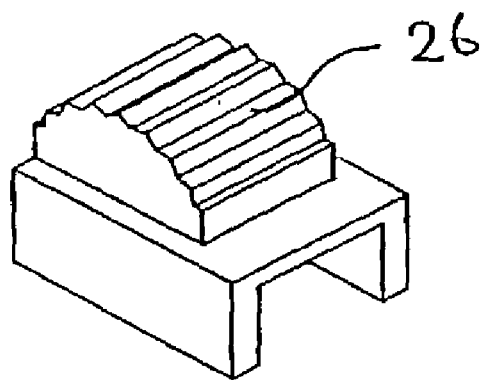
FIG. 7 illustrates a locking portion of the tensioner.

FIG. 6 illustrates detail of the tensioner 9. Tensioner 9 includes a locking member 26, which is illustrated in FIG. 7. Tensioner 9 comprises a body 27 extending to clamp 10 at one end. The tensioner 9 is also made from thermoplastic elastomers (TPEs) to provide flexibility with good elastic recovery properties. Body 27 is formed with a substantially 'hat' shaped cross-section having outwardly extending rails 28, 29 along either edge. The end 30 of tensioner 9 is hollow thereunder and has an opening 31 for receiving locking member 26. Centrally on tensioner 9 is a grip 32 with which a user can slidably move tensioner 9 on handle 3. Extending from the grip 32 in to hollow end 30 is a locking tab 37.

The clamp 10 of tensioner 9 comprises a central body member 33 having corrugated mating surfaces formed in either side. Extending in an outwardly direction, away from each other, on either side of central body member 33 at two clamping arms 34, 35. The two clamping arms 34, 35 have corresponding corrugated mating surfaces and are deformably movable in an inwards direction so that their corresponding corrugated mating surface engages with the respective mating surface of central body member 33 to provide jaws 11, 12.

Tensioner 9 is slidably receivable within the channel 21 of handle 3. Rails 28, 29 of tensioner 9 slidably engage within grooves 22, 23 of channel 21. The tensioner 9 is slidably movable to a first position wherein clamp 10 extends beyond the mouth of channel 21 proximate head 4. In this position clamp arms 34, 35 are in their natural outwardly extending position opening jaws 11, 12 of clamp 10. In use, a length 2 of flossing string is drawn loosely between distal ends 6 and 8 of head arms 5 and 7. One end 13 of flossing string 2 is laid in the groove 15 of arm 5 and through open jaw 11 of clamp 10. The other end of 14 of flossing string 2 is laid in groove 16 of arm 7 and through open jaw 12 of clamp 10. This arrangement is illustrated in FIG. 1.

Referring again to FIG. 2, tensioner 9 can be slidably moved back along channel 21 of handle 3. As tensioner 9 is slidably moved clamp 10 is drawn into the mouth of channel 21. The shoulders 24, 25 of the mouth engage against clamp arms 34, 35 respectively closing jaws 11 and 12 to clamp ends 13, 14 of flossing string 2 therein. As tensioner 9 is slidably moved further along channel 21 tension is applied to flossing string 2 drawing it taught between distal ends 6, 8 of arms 5, 7. Arms 5, 7 flexibly deform inwardly under tension.

Figure 8:
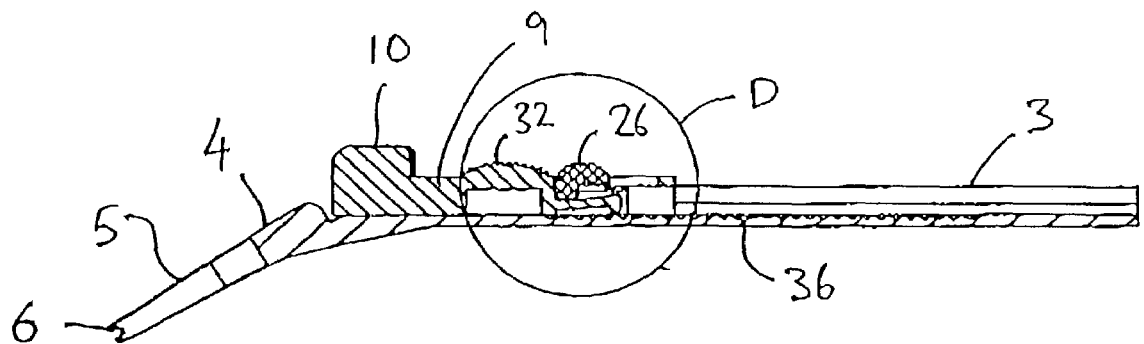
FIG. 8 illustrates a sectional side elevation view of the handle and head portion with tensioner.
Figure 9:
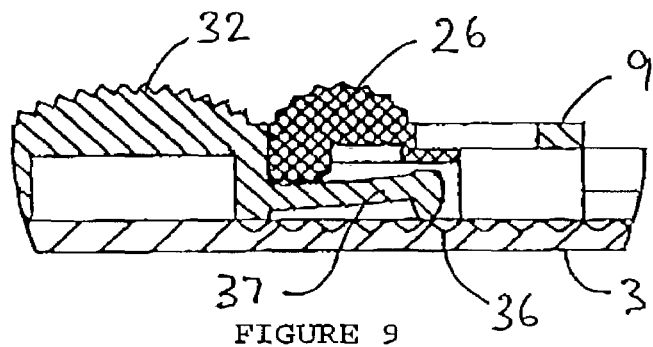
FIG. 9 is a first detailed illustration of area D of FIG. 8.
Figure 10:
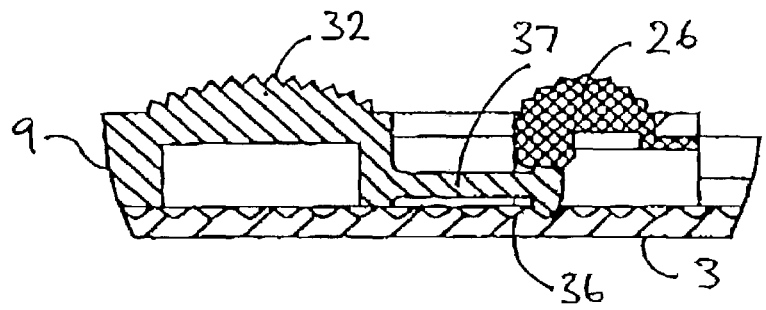
FIG. 10 is a second detail illustration of area D of FIG. 8.

FIGS. 8 to 10 illustrate how lock 26 is slidably moved within hollow end 30 of tensioner 9 to cause locking tab 37 to engage with locking teeth 36. Locking member 26 is slidably moved to a position adjacent grip portion 32. In this position locking tab 37 is free to move over locking teeth 36 as tensioner 9 is slidably moved within channel 21. When the tensioner 9 has been moved to apply the desired attention to flossing string 2, locking member 26 is slidably moved away from the grip 32 causing locking tab 37 to engage with locking toothed 36 to lock tensioner 9 in position. Such locking arrangements are common in the art and a variety of methods are known. Typical examples are found in the wide variety of retractable blade utility knives common in the market.

The flossing tool of the invention is easy to operate and manipulate. When the flossing string between the distal ends 6, 8 of arms 5, 7 becomes dirtied the user may slidably move tensioner 9 forward, to release the jaws 11, 12 of clamp 10, and draw the flossing string 2 through the jaws 11, 12 to position a clean portion of flossing string 2 between distal ends 6, 8. Tensioner 9 is then slidably moved back again to retention the flossing string 2.

Figure 11:
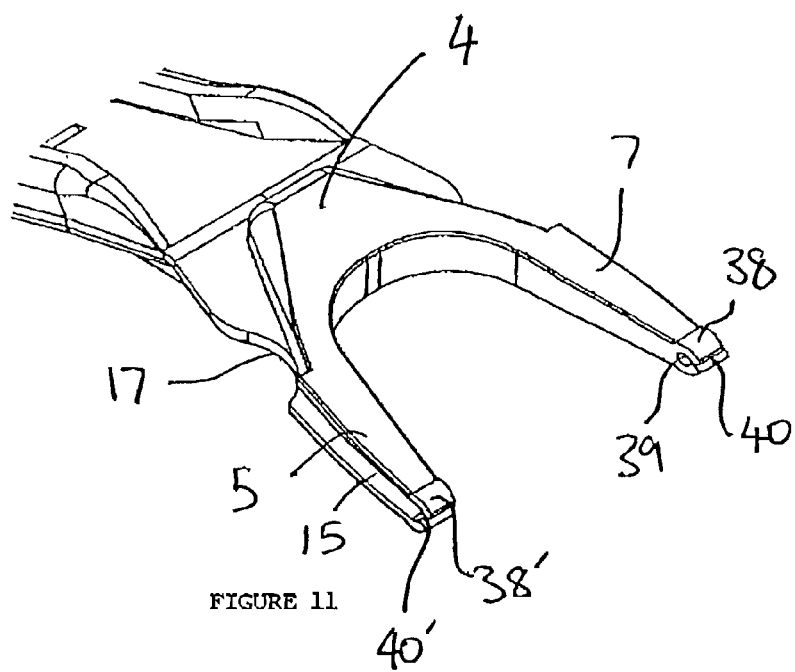
FIG. 11 is a second embodiment of the head of the flossing tool.

Referring to FIG. 11, the distal ends 6, 8 of arms 5, 7 has a split eye 38. The eye 38 retains the flossing string 2 which might fall out of groves 15, 16 when the string is not under tension. Threading flossing string through a hole 39 in the eye 38 might prove awkward. However a split 40 in the eye wall allows the flossing string to be pulled into the eye 38. The split 40 is under tension and thus the floss will not fall out of the eye 38 unless it is pulled back through the split 40.

Figure 12:
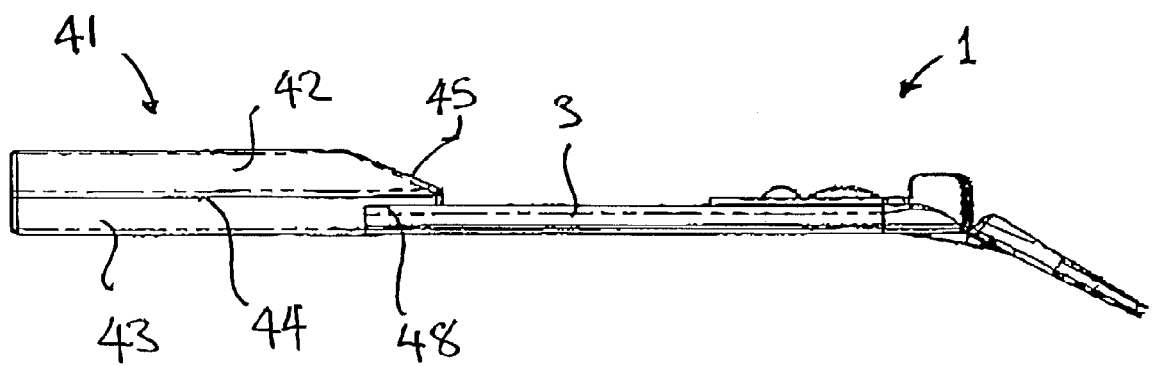
FIG. 12 is a cartridge for holding a length of flossing string.
Figure 13:
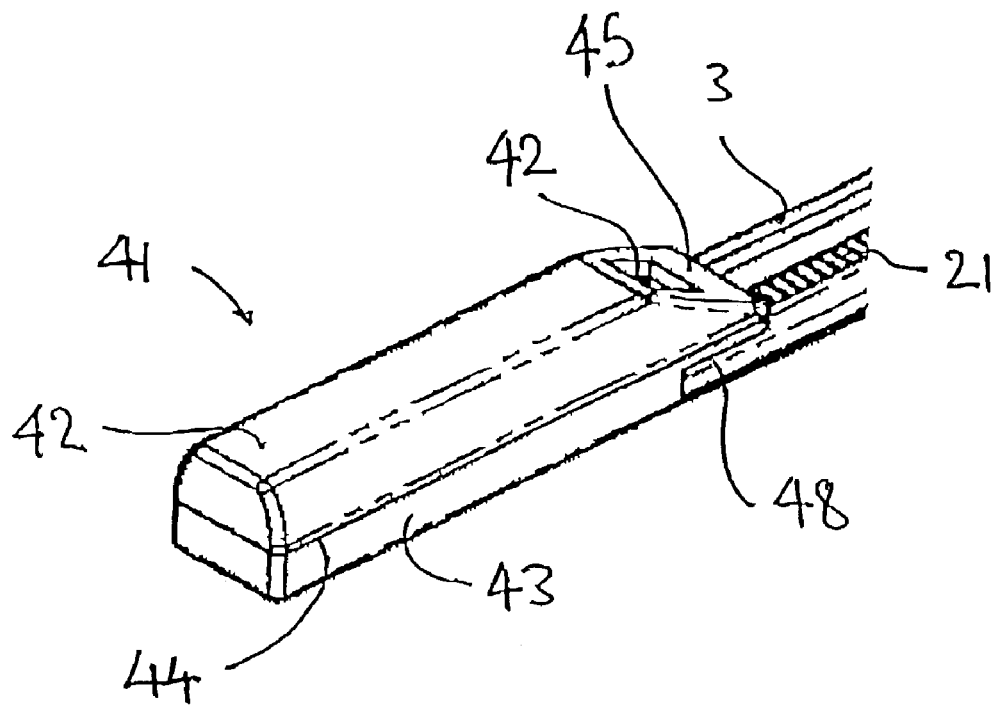
FIG. 13 is a perspective view of the cartridge.
Figure 14:
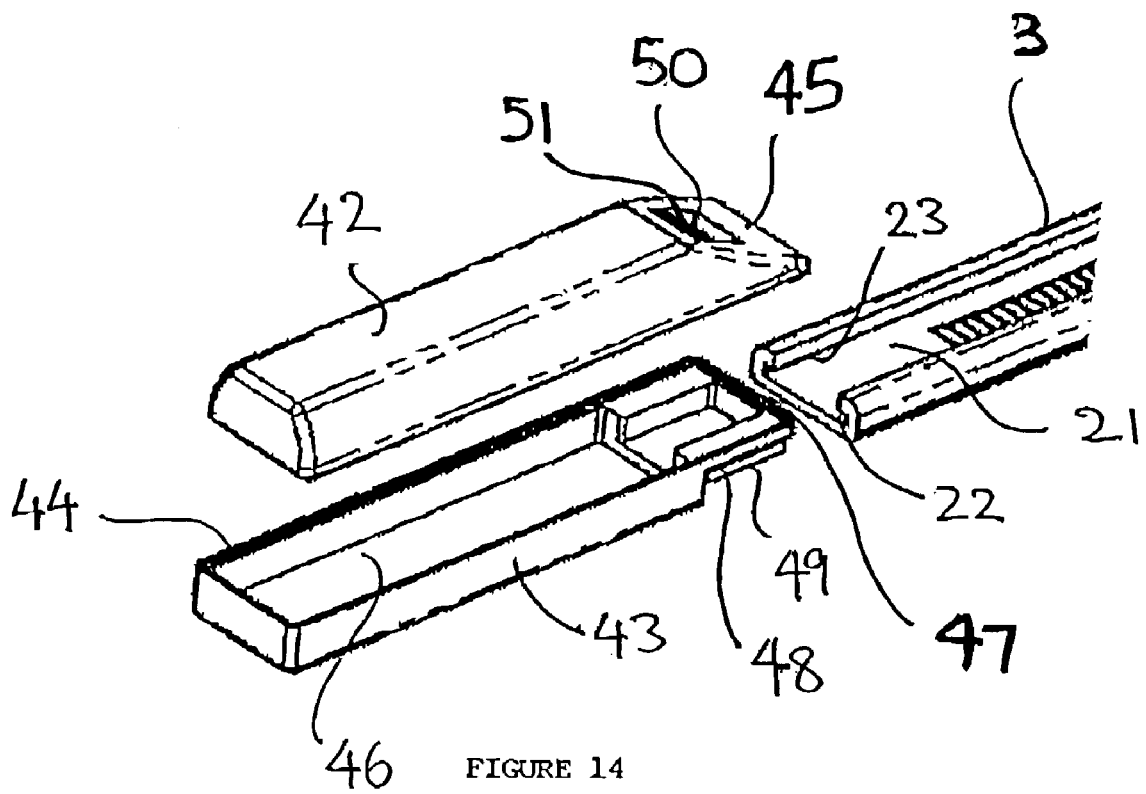
FIG. 14 is an exploded view of the cartridge.

Referring to FIGS. 12 to 14, a cartridge 41 is optionally provided for enclosing a length of flossing string for use with the flossing tool. The cartridge 41 removably attaches to the distal end of handle 3.

Cartridge 41 comprises an upper housing 42 and the lower housing 43 joined at an equator 44 to provide an internal cavity 46 into which a quantity of flossing string can be accommodated. The housing portions 42, 43 releasably join at equator 44 by clips or other known means so they can be separated for inserting and removing a length of flossing string. The front 45 of upper housing 42 is tapered. Located on the taper is an opening 50 through which flossing string passes to the threaded through the flossing tool as previously described.

The front portion 47 of lower housing 43 has a stepped in portion 48. The stepped in portion 48 has rails 49 which receivably engage within groves 22, 23 of channel 21 to releasably secured cartridge 41 to the distal end of handle 3.

Cartridge 41 provides a mean to store a length of flossing string 2 conveniently with the device. An end of the flossing string can be brought out through hole 50 threaded through jaws 11, 12 and around head 4 of the device as previously described. As the flossing string is used and discarded more flossing string can be brought through opening 50.

A blade 51 is provided along one edge of opening 50 for cutting the flossing string.

In an alternative embodiment the cartridge 41 is a sealed unit and does not separate at equator 44. The sealed unit can be sold separately from the flossing tool and contains flossing string. When all of the flossing string in the cartridge 44 is used the cartridge is disposed of and a new cartridge purchased.

Where in the foregoing description reference has been made to integers or elements having known equivalents then such are included as if individually set forth herein.

Embodiments of the invention have been described, however it is understood that variations, improvement or modifications can take place without departure from the spirit of the invention or scope of the appended claims.

What is claimed is:

1. A flossing tool for use with flossing string, the flossing tool including:
   a handle having first and second ends;
   a head at the first end of the handle and having a first arm extending outwardly to a first distal end and a second arm extending outwardly to a second distal end, the first and second distal ends adapted to support flossing string therebetween, and
   a tensioner slidable longitudinally on the handle and having a clamp with jaws, the tensioner being movable between a first position for freely receiving ends of the flossing string in the jaws and a second position for securing the ends of the flossing string in the jaws, the tensioner further movable longitudinally on the handle to tension the flossing string.

2. The flossing tool of claim 1 wherein the first arm has a first groove for guiding the flossing string to the first distal end, and second arm has a second groove for guiding the flossing string to the second distal end.

3. The flossing tool of claim 1 wherein the first and second arms extend outwardly away from each other.

4. The flossing tool of claim 3 wherein the first and second arms resiliently deform inwardly towards each other.

5. The flossing tool of claim 1 wherein the handle has a channel extending from proximate its first end towards its second end for slidably receiving the tensioner.

6. The flossing tool of claim 1 wherein the first and second distal ends have a split eye.

7. The flossing tool of claim 1 further including a cartridge releasably mounted to the handle for holding flossing string.

8. The flossing tool of claim 7 wherein the cartridge comprises first and second housing elements releasably joined at an equator, and an opening through which flossing string can pass.

9. The flossing tool of claim 8 wherein the opening is provided with a blade for cutting the flossing string.

10. The flossing tool of claim 1 wherein the clamp jaws comprises side-by-side jaws.

11. A flossing tool for use with flossing string, the flossing tool including:
    a handle portion having a first end and a second end;
    a head at the first end of the handle and having a first arm extending outwardly to a first distal end and a second arm extending outwardly to a second distal end, the first and second distal ends adapted to support flossing string there between,
    a channel extending longitudinally from the first and second ends of the handle, and
    a tensioner slidably positioned with the channel and having a with side-by-side jaws, the tensioner being longitudinally movable between a first position for freely receiving ends of the flossing string in the jaws and a second position for securing the ends of the flossing string in the jaws and the tension further longitudinally movable on the handle for tensioning the flossing string between the first and second distal ends.

* * * * *